(12) United States Patent
Rampf et al.

(10) Patent No.: US 8,227,641 B2
(45) Date of Patent: Jul. 24, 2012

(54) PROCESS FOR THE PREPARATION OF AMINOALKYLAMINES

(75) Inventors: Florian Rampf, Hegenheim (FR); Guido Giffels, Bonn (DE)

(73) Assignee: SALTIGO GmbH, Langenfeld (DE)

( * ) Notice: Subject to any disclaimer, the term of this patent is extended or adjusted under 35 U.S.C. 154(b) by 319 days.

(21) Appl. No.: 12/520,877

(22) PCT Filed: Dec. 12, 2007

(86) PCT No.: PCT/EP2007/063798
§ 371 (c)(1),
(2), (4) Date: Jan. 4, 2010

(87) PCT Pub. No.: WO2008/080784
PCT Pub. Date: Jul. 10, 2008

(65) Prior Publication Data
US 2010/0145102 A1    Jun. 10, 2010

(30) Foreign Application Priority Data
Dec. 27, 2006  (DE) .......................... 10 2006 061 535

(51) Int. Cl.
*C07C 209/48*   (2006.01)
(52) U.S. Cl. ...................................... 564/491
(58) Field of Classification Search ........... 564/491
See application file for complete search history.

(56) References Cited

FOREIGN PATENT DOCUMENTS

| EP | 0382508 A2 * | 8/1990 |
| EP | 0707611 | 7/1994 |
| WO | WO 95/02008 | 1/1995 |

\* cited by examiner

*Primary Examiner* — Brian J Davis
(74) *Attorney, Agent, or Firm* — Michael A. Miller

(57) ABSTRACT

Process for the preparation of polyfunctional amines of the formulae

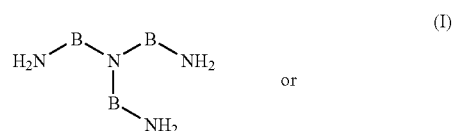

or

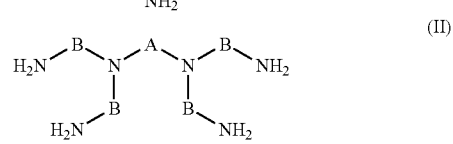

by hydrogenation of the associated nitriles of the formulae

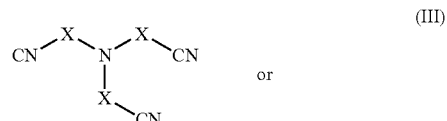

or

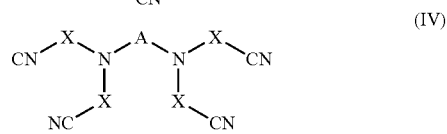

with hydrogen, where
A is an aromatic or aliphatic compound from the group of unsubstituted or substituted phenylene or naphthylene, methylene, unsubstituted or substituted ethylene, propylene, unsubstituted or substituted straight-chain or branched butylene, pentylene, hexylene, heptylene, octylene, nonylene, decylene and
B is a straight-chain or branched aliphatic carbon chain having 1 to 10 carbon atoms, and
X can be missing or is a straight-chain or branched aliphatic carbon chain having 1 to 10 carbon atoms,
wherein a melt, solution or suspension of the nitrile of formula (III) or (IV) is added over the course of the reaction time to a suspension or solution of a catalyst in a solvent which comprises ammonia and is stirred at a temperature range from 60 to 150° C. under hydrogen pressure.

8 Claims, No Drawings

PROCESS FOR THE PREPARATION OF AMINOALKYLAMINES

The invention relates to the preparation of aminoalkylamines such as e.g. tetra-N,N,N',N'-(3-aminopropyl)-1,4-diaminobutane.

Tetra-N,N,N',N'-(4-aminopropyl)-1,4-diaminobutane is a hexamine which can be used as complexing agent, as monomer or as core molecule for the preparation of dendrimers. It is effective as complexing agent through the possibility of bonding metal ions to the nitrogen atoms via the free electron pairs. It can be used as monomer because can react as tetrafunctional primary amine with polyfunctional electrophiles to give polymeric structures. One special form of a polymer is dendrimers in which tetra-N,N,N',N'-(3-aminopropyl)-1,4-diaminobutane forms tree-like structures through repeated reaction steps in a controlled manner.

An industrially applicable synthesis of tetra-N,N,N',N'-(3-aminopropyl)-1,4-diaminobutane is described in the patent literature. WO 95/2008 and EP-A 707 611 describe the preparation of tetra-N,N,N',N'-(3-aminopropyl)-1,4-diaminobutane starting from 1,4-diaminobutane through four-fold reaction with acrylonitrile to give tetra-N,N,N',N'-(2-cyanoethyl)-1,4-diaminobutane and subsequent hydrogenation. The hydrogenation is carried out in the cited publications over heterogeneous Raney metal catalysts in the presence of ammonia in alcoholic solvents. According to the cited process, the hydrogenations are thus carried out by initially introducing tetra-N,N,N',N'-(2-cyanoethyl)-1,4-diaminobutane in an alcoholic solvent with the—freed from water by washing—catalyst, then adding ammonia, injecting hydrogen and adjusting the reaction temperature. At the end of the reaction time, the hydrogen pressure is let down, filtered off from the catalyst and the product is separated from the solvent by distillation.

The disadvantage of the described process is that it requires the use of very large amounts of the described Raney catalysts. The lowest described catalyst amount is 12.3% by weight of dry catalyst, based on the weight of the tetra-N,N,N',N'-(2-cyanoethyl)-1,4-diaminobutane used. In further examples, up to 51.8% by weight of dry catalyst are used. Since this catalyst is supplied as moist suspension with a water fraction of 50%, catalyst quantities of ca. 25 up to more than 100% by weight of the amount of tetra-N,N,N',N'-(2-cyanoethyl)-1,4-diaminobutane used are required in order to obtain the desired product. This precludes an efficient and economical process conversion and makes desirable a process which produces a similarly good quality of the product when using smaller amounts of catalyst.

It was therefore an object of the invention to provide a process for the preparation of aminoalkylamines which is more efficient and more economical.

Surprisingly, it has now been found that tetra-N,N,N',N'-(3-aminopropyl)-1,4-diaminobutane can be prepared in high purity with the use of significantly less catalyst if the solution of tetra-N,N,N',N'-(2-cyanoethyl)-1,4-diaminobutane is added under hydrogenation conditions to a mixture of Raney catalyst and solvent, ammonia and hydrogen continuously and in an amount which is consumed by the reaction.

The invention consists in a process for the preparation of polyfunctional amines of the formulae (I) or (II)

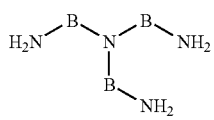

(I)

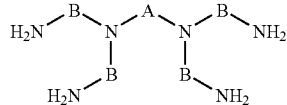

(II)

by hydrogenation of the associated nitriles of the formulae (III) or (IV)

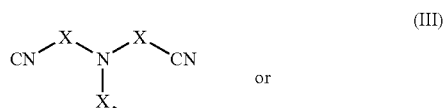

(III)

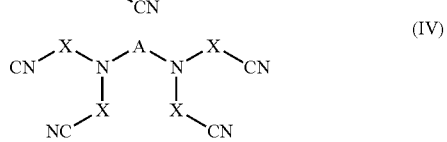

(IV)

where
A is an aromatic or aliphatic compound from the group of unsubstituted or substituted phenylene or naphthylene, methylene, unsubstituted or substituted ethylene, propylene, unsubstituted or substituted straight-chain or branched butylene, pentylene, hexylene, heptylene, octylene, nonylene, decylene and B is a straight-chain or branched aliphatic carbon chain, such as methylene, unsubstituted or substituted ethylene, propylene, unsubstituted or substituted straight-chain or branched butylene, pentylene, hexylene, heptylene, octylene, nonylene, decylene, where at least one $CH_2$ unit must be in direct vicinity to the amino group, and X can be missing or is a straight-chain or branched aliphatic carbon chain, such as methylene, unsubstituted or substituted ethylene, propylene, unsubstituted or substituted straight-chain or branched butylene, pentylene, hexylene, heptylene, octylene, nonylene, decylene, characterized in that a melt, solution or suspension of the nitrile according to formula (III) or (IV) is pumped over the course of the reaction time to a suspension or solution of the catalyst in a solvent which comprises ammonia and optionally other additives for increasing the selectivity and is stirred at a reaction temperature in the range from 60 to 150° C. under hydrogen pressure.

Preference is given to using the nitriles of the formula (III) or (IV) in which

X is an ethylene group and
A is selected from the group methylene, ethylene, propylene, n-butylene, n-pentylene, n-hexylene.

These produce, by hydrogenation, amines of the formula (I) and (II) in which

B is a propylene group and
A is selected from the group methylene, ethylene, propylene, n-butylene, n-pentylene, n-hexylene.

Before the reaction, the nitriles are either melted or dissolved or suspended in a suitable solvent. Suitable solvents are those which are usually used for hydrogenations, in particular water, alcohols, cyclic or open-chain ethers, halogenated or nonhalogenated aliphatic or aromatic hydrocarbons. Preference is given to using water or alcohols, and particularly preferably alcohols such as methanol, ethanol, isopropanol or mixtures of these alcohols with water in a mixing ratio of water to alcohol of 1:50 to 10:1.

The reaction is carried out, for example, in a closed pressurized vessel which has a stirrer device. A continuous procedure in a tubular reactor is likewise conceivable.

The hydrogenation is carried out in the presence of hydrogen gas. In order to ensure a complete reduction of the nitrile groups, it is necessary to provide an adequate amount of hydrogen. Per nitrile group, at least an amount of two equivalents of hydrogen is required. An adequate amount of hydrogen is usually achieved by injecting the hydrogen under pressure. In the process according to the invention, the hydrogen is initially introduced in the reactor under pressure prior to the start of the reaction. Preferably, hydrogen is initially introduced under a pressure of from 10 to 200 bar, particularly preferably under a pressure of from 50 to 150 bar.

The pressure in the reactor is furthermore brought about by the presence of ammonia. Ammonia serves to control the selectivity of the hydrogenation so that preferably primary amines are formed. In the absence of ammonia, according to experience, secondary and tertiary amines are formed as by-products of the reaction. The molar ratio between ammonia and nitrile groups in the starting material should be between 0.25 and 2 mol of ammonia per mole of nitrile group, preferably between 0.65 and 1.25.

Further additives can lilkewise serve to increase the selectivity of the reaction for primary amines. For example, basic additives such as sodium hydroxide or potassium hydroxide or calcium oxide are suitable.

The temperature of the reaction is adjusted to values of from 60 to 150° C., preferably to values of from 80 to 120° C.

The hydrogenation is carried out in the presence of a suitable catalyst. For this, a hydrogenation catalyst is usually used, preferably a heterogeneous hydrogenation catalyst. The catalysts used can originate from group VIII of the Periodic Table of the Elements which, as is known, exhibit hydrogenation activity toward nitriles. Of particular suitability are nickel, cobalt, platinum, palladium and rhodium, particularly in fauns which have a high active surface area. For this, the metal can be applied in a thin layer, for example, on a support material. So-called Raney catalysts such as Raney nickel or Raney cobalt are particularly suitable. These catalysts are known to the person skilled in the art and commercially available from several manufacturers.

Raney nickel and Raney cobalt are alloys of nickel or cobalt with aluminium. They can contain additives of other metals such as chromium or iron in order to increase their activity or selectivity. Particularly the addition of chromium is advantageous for a high activity in the hydrogenation of nitriles.

Raney catalysts are often supplied as aqueous suspension. Within the context of the invention, the catalyst can be used either water-moist, or else the water in the supply form is exchanged for a solvent by washing. Suitable solvents are the solvents already mentioned above which can also serve for the pumping in of the nitrile.

According to the invention, the optionally washed catalyst is initially introduced into the reactor, together with solvent, hydrogen and ammonia and stirred under the reaction conditions.

The amount of catalyst used is initially dependent on the geometry and the handling of the reactor used. Moreover, it is governed by the amount of substrate to be hydrogenated. Surprisingly, it has now been found that the amount of catalyst required compared to the prior art can be reduced by ca. half, with the selectivity and activity of the catalyst not being reduced. WO 95/2008 and EP-A 707 611 describe the use of 12 to 50% by weight of the starting material over dry catalyst as required amount. According to the process of the invention, just 5-8% by weight of the starting material over dry catalyst suffice to ensure complete conversion of the nitrile according to formula (III) and (IV) with almost complete selectivity in favour of the amines according to formula (I) and (II).

The content of the reactor must be carefully mixed so that both sufficient hydrogen is introduced into the reaction mixture and the catalyst is adequately circulated in order to be able to interact with the starting material. For this, stirring devices within the reactor are suitable.

The reaction is started by pumping the melt, the solution or the suspension of the starting material into the reactor against the hydrogen pressure. The reaction takes place spontaneously following the dropwise introduction of the starting material. The reaction time is determined largely by the duration of the pumping operation. Usually, pumping is carried out within a period from 30 min to 24 h, preferably within 1 h to 8 h. When the pumping operation is complete, the continued absorption of hydrogen can occur, caused by the reaction which has not yet completely concluded. When hydrogen absorption has finished, the reaction is ended. Typical post-reaction times are between 5 min and 4 h.

After the reaction, the catalyst used is filtered off from the reaction mixture. This can take place via a filter unit outside of the reactor or by filter candles and a riser tube inside the vessel. Thus, the catalyst can either be fed to a suitable disposal or else to recycling. For the recycling, the catalyst can either remain in the reactor and be used again immediately, or else it is reactivated prior to the next use. For the reactivation, the catalyst can, for example, be washed with an aqueous solution of NaOH or KOH at elevated temperature and be afterwashed with water until the solution which runs off is almost neutral.

EXAMPLES

Example 1

720 g of tetra-N,N,N',N'-(2-cyanoethyl)-1,4-diaminobutane were dissolved in 720 g of methanol. 96 g of water-moist Raney cobalt catalyst, e.g. Raney 2724 from Grace (corresponds to 48 g of dry catalyst) were washed at room temperature 3× with in each case 100 ml of methanol and transferred with 320 ml of methanol to a 3 l autoclave made of VA steel. The autoclave was closed, the atmospheric oxygen was displaced by injecting nitrogen three times, then 200 g of ammonia were forced in with continuing stirring. Then, the mixture was heated to 95° C. with stirring and the internal pressure was increased to 100 bar with hydrogen. Using a LEWA high-pressure membrane pump, the reaction solution was pumped into the autoclave in 4 hours while the reaction mixture was stirred vigorously. At the end of dosing, the mixture was stirred for a further 15 min, then cooled to 25° C. and decompressed, and the content of the autoclave was filtered off from the autoclave with the exclusion of air (fire hazard due to active catalyst). The methanolic solution which is formed was concentrated on a rotary evaporator at 80° C. and 20 mbar. 735 g of tetra-N,N,N',N'-(3-aminopropyl)-1,4-diaminobutane were left behind. The purity was 97% according to GC.

The invention claimed is:

1. A process for the preparation of polyfunctional amines of the formulae

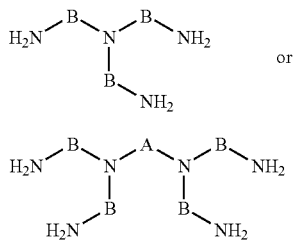
(I)

or

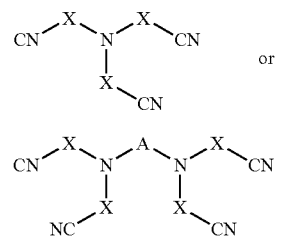
(II)

by hydrogenation of the associated nitriles of the formulae (III)

(IV)

with hydrogen, where

A is an aromatic or aliphatic compound selected from the group consisting of unsubstituted or substituted phenylene or naphthylene, methylene, unsubstituted or substituted ethylene, propylene, unsubstituted or substituted straight-chain or branched butylene, pentylene, hexylene, heptylene, octylene, nonylene, and decylene and B is a straight-chain or branched aliphatic carbon chain having 1 to 10 carbon atoms, and X can be missing or is a straight-chain or branched aliphatic carbon chain having 1 to 10 carbon atoms, characterized in that a melt, solution or suspension of the nitrile of the formula (III) or (IV) is added over the course of the reaction time to a suspension or solution of a catalyst in a solvent selected from the group of alcohol, water or mixtures of alcohol and water which comprises ammonia and is stirred at a temperature in the range from 60 to 150° C. under hydrogen pressure.

2. The process according to claim 1, characterized in that the catalyst is a hydrogenation catalyst comprising nickel, cobalt, platinum, palladium or rhodium, optionally on a support material.

3. The process according to claim 1, characterized in that the molar ratio between ammonia and nitrile group in starting material is 0.25 to 2.00.

4. The process according to one of claim 1, characterized in that the hydrogen pressure is between 10 and 200 bar.

5. The process according to one claim 1, characterized in that the solvent is water, methanol, ethanol, isopropanol or a mixture of these alcohols with water.

6. The process according to claim 1, characterized in that X is an ethylene group and A is a methyl, ethyl, propyl, n-butyl, n-pentyl or n-hexyl group.

7. The process according to claim 1, characterized in that sodium hydroxide, potassium hydroxide or calcium oxide are added as additives.

8. The process according to claim 1, characterized in that the temperature is between 80 and 120° C.

* * * * *